(12) United States Patent
Keary et al.

(10) Patent No.: US 8,383,198 B2
(45) Date of Patent: Feb. 26, 2013

(54) WATER DISPERSIBLE POLYMER COMPOSITIONS

(75) Inventors: Colin M. Keary, Midland, MI (US); Paul J. Sheskey, Midland, MI (US); Karen M. Balwinski, Bay City, MI (US)

(73) Assignee: Dow Global Technologies LLC, Midland, MI (US)

( * ) Notice: Subject to any disclaimer, the term of this patent is extended or adjusted under 35 U.S.C. 154(b) by 127 days.

(21) Appl. No.: 12/599,179

(22) PCT Filed: Feb. 28, 2008

(86) PCT No.: PCT/US2008/055283
§ 371 (c)(1),
(2), (4) Date: Nov. 6, 2009

(87) PCT Pub. No.: WO2008/140853
PCT Pub. Date: Nov. 20, 2008

(65) Prior Publication Data
US 2010/0221546 A1    Sep. 2, 2010

Related U.S. Application Data

(60) Provisional application No. 60/928,182, filed on May 8, 2007.

(51) Int. Cl.
*B01J 13/02* (2006.01)

(52) U.S. Cl. .................. 427/213.3; 106/122; 106/162.1; 106/163.01; 427/212; 427/213.35; 427/430.1; 428/402; 428/402.24; 428/403; 428/407; 523/205

(58) Field of Classification Search ............ 427/212, 427/213.3, 213.35, 430.1; 106/122, 162.1, 106/163.01; 428/402, 403, 407, 402.24; 523/205
See application file for complete search history.

(56) References Cited

U.S. PATENT DOCUMENTS

| | | | |
|---|---|---|---|
| 3,607,364 A | 9/1971 | Lopez et al. | |
| 4,476,145 A | 10/1984 | Hardie-Muncy et al. | |
| 4,626,287 A * | 12/1986 | Shah et al. | 106/162.8 |
| 4,671,823 A | 6/1987 | Shah et al. | |
| 4,735,659 A | 4/1988 | Bishop | |
| 5,026,735 A | 6/1991 | Stern | |
| 5,204,087 A | 4/1993 | Moroi et al. | |
| 5,266,334 A | 11/1993 | Phadke et al. | |
| 5,766,638 A * | 6/1998 | Tobey | 424/499 |
| 6,468,957 B1 | 10/2002 | Larson et al. | |
| 6,500,462 B1 * | 12/2002 | Augello et al. | 424/490 |
| 6,683,042 B1 | 1/2004 | Larson et al. | |
| 7,011,702 B2 | 3/2006 | Sheskey et al. | |
| 7,070,828 B2 | 7/2006 | Sheskey et al. | |
| 7,425,236 B2 | 9/2008 | Yu et al. | |
| 2004/0023012 A1 | 2/2004 | Kia et al. | |
| 2004/0241247 A1 | 12/2004 | Sheskey et al. | |
| 2005/0186271 A1 | 8/2005 | Sheskey et al. | |
| 2005/0202176 A1 | 9/2005 | Brady et al. | |

FOREIGN PATENT DOCUMENTS

| | | |
|---|---|---|
| CA | 2300494 A1 | 11/2000 |
| DE | 19910789 A1 | 11/1999 |

* cited by examiner

*Primary Examiner* — John Cooney

(57) ABSTRACT

The water dispersibility of water-soluble polymer particles can be improved by a method which comprises the following step: i) foaming a fluid composition comprising a compound A) having a weight average molecular weight of less than 10,000 or a water-insoluble polymer B) having a weight average molecular weight of at least 10,000; ii) contacting the produced foam with water-soluble polymer particles having a weight average molecular weight of at least 10,000; and iii) drying the particles, whereby the foam collapses during the contacting and/or drying step and the water-soluble polymer particles are encrusted with the compound having a weight average molecular weight of less than 10,000 or the water-insoluble polymer having a weight average molecular weight of at least 10,000.

4 Claims, No Drawings

WATER DISPERSIBLE POLYMER COMPOSITIONS

CROSS REFERENCE TO RELATED APPLICATIONS

This application is a 35 USC §371 national phase filing of PCT/US2008/055283 filed 28 Feb. 2008, which claims the benefit of Application No. 60/928,182, filed 8 May 2007.

BACKGROUND OF THE INVENTION

This invention relates to compositions of water soluble polymers and a method of improving their dispersibility in water.

Water soluble polymers are conventionally utilized in the form of dilute aqueous solutions. Although the polymers as manufactured can be dispersed in water to provide homogeneous solutions, care must be exercised in achieving an initial dispersion of the polymer in water. Unless proper precautions are taken, the polymer is likely to agglomerate upon wetting with water to form partially hydrated agglomerated polymer which is slow to dissolve. Moreover, the agglomerated polymer has a tendency to plug liquid handling equipment. Although complete dissolution of the agglomerated polymer is possible its achievement may require extended periods of time or special treatments to promote rapid dissolution of the gels. Removal of the agglomerated polymer from solutions is also an alternative but is wasteful of polymer. Accordingly, much effort has been spent by the skilled artisans to improve the dispersibility of water-soluble polymers in water.

U.S. Pat. No. 4,735,659 teaches coating of water-soluble polymers with hydrophobic fumed silica to improve the water dispersibility of the polymer. The coating is said to be effected by simply blending the water-soluble polymer with the hydrophobic fumed silica.

U.S. Pat. No. 4,671,823 discloses that cellulose ethers are effective bulk laxatives which are administered in the form of tablets, as powders or as suspensions. The disadvantages of these forms of administration are discussed in these patents, as well as the need to provide a cellulose ether composition which is palatable and which is administered without the formation of significant amounts of lumps or gels. In order to solve the problem of lump and gel formation U.S. Pat. No. 4,671,823 teaches a process wherein powdered cellulose ether is mixed with hot sucrose syrup until an evenly moist product is formed which is then dried and milled. The amount of sucrose is 20-90 percent of the weight of the resulting encrusted particle.

U.S. Pat. No. 5,266,334 discloses water-dispersible sugar-free bulk laxative compositions which comprise a dry mixture of a) an edible, water-soluble cellulose ether having efficacy as a bulk laxative, b) a sugar-free sweetening component and c) a dispersing agent. A preferred dispersing agent is maltodextrin.

U.S. Pat. No. 4,321,263 discloses the use of psyllium as a bulk laxative. It discusses the tendency of psyllium to form lumps in water and the use of sugar as a means of promoting dispersion ease. The U.S. patent teaches that psyllium powder is rendered rapidly dispersible in water by wetting the psyllium particles with an alcoholic solution of polyethylene glycol or polyvinylpyrrolidone and granulating the thus-coated particles.

Although the above-mentioned methods improve the water dispersibility of water-soluble polymers it would be desirable to further improve their water dispersibility. It would be particularly desirable to improve the water dispersibility of water-soluble polymers without substantially increasing the amount of a dispersing agent, such as maltodextrin or sucrose, or to reduce the amount of a dispersing agent, such as maltodextrin or sucrose, without substantially decreasing the water dispersibility of water-soluble polymers.

SUMMARY OF THE INVENTION

One aspect of the present invention is a water dispersible polymer composition wherein water-soluble polymer particles having a weight average molecular weight of at least 10,000 are encrusted with a dried, non-foamed residue of a foamed fluid comprising a compound A) having a weight average molecular weight of less than 10,000 or a water-insoluble polymer B) having a weight average molecular weight of at least 10,000.

Another aspect of the present invention is a water dispersible polymer composition wherein water-soluble polymer particles having a weight average molecular weight of at least 10,000 are encrusted with I) a compound A) having a weight average molecular weight of less than 10,000 or a water-insoluble polymer B) having a weight average molecular weight of at least 10,000; and II) a foaming agent other than the compound A) or the water-insoluble polymer B).

Yet another aspect of the present invention is a water dispersible polymer composition wherein water-soluble polymer particles having a weight average molecular weight of at least 300,000 are encrusted with a dried, non-foamed residue of a foamed fluid comprising a water-soluble polymer having a weight average molecular weight of less than 100,000.

Yet another aspect of the present invention is a water dispersible polymer composition wherein water-soluble polymer particles having a weight average molecular weight of at least 300,000 are encrusted with I) a water-soluble polymer having a weight average molecular weight of less than 100,000; and II) a foaming agent other than the water-soluble polymer having a weight average molecular weight of less than 100,000.

Yet another aspect of the present invention is a process for producing a water dispersible polymer composition, which process comprises the steps of i) foaming a fluid composition comprising a compound A) having a weight average molecular weight of less than 10,000 or a water-insoluble polymer B) having a weight average molecular weight of at least 10,000; ii) contacting the produced foam with water-soluble polymer particles having a weight average molecular weight of at least 10,000; and iii) drying the particles, whereby the foam collapses during the contacting and/or drying step and the water-soluble polymer particles are encrusted with the compound A) or the water-insoluble polymer B).

Yet another aspect of the present invention is a method of improving the water dispersibility of water-soluble polymer particles, which method comprises the steps i)-iii) in the preceding paragraph.

Yet another aspect of the present invention is a process for producing process for producing a water dispersible polymer composition, which process comprises the steps of i) foaming a fluid composition comprising a water-soluble polymer having a weight average molecular weight of less than 100,000; ii) contacting the produced foam with water-soluble polymer particles having a weight average molecular weight of at least 300,000; and iii) drying the particles, whereby the foam collapses during the contacting and/or drying step and the water-soluble polymer particles having a weight average molecular weight of at least 300,000 are encrusted with the water-soluble polymer having a weight average molecular weight of less than 100,000.

Yet another aspect of the present invention is a method of improving the water dispersibility of water-soluble polymer particles, which method comprises the steps i)-iii) in the preceding paragraph.

DETAILED DESCRIPTION OF THE INVENTION

As discussed in the Background of the Invention above, it is known in the prior art that the water dispersibility of water-soluble polymer particles can be improved when the water-soluble polymer particles are contacted with a coating, such as hydrophobic fumed silica, polyethylene glycol or polyvinylpyrrolidone; a dispersing agent, such as maltodextrin, or an encrustant, such as sucrose. Such coatings, dispersing agents or encrustants are hereafter collectively designated as "encrustant". They are applied to the water-soluble polymer particles by dry-blending, as an alcoholic solution or as a hot aqueous solution.

Surprisingly, it has been found that the water dispersibility of water-soluble polymer particles can be further improved when the encrustant is contacted with the polymer particles as a foamed fluid and the particles are dried, whereby the foam collapses during the contacting and/or drying step. The improved water dispersibility is evidence that a water dispersible polymer composition of different physical structure is produced when the encrustant is contacted with the polymer particles as a foamed fluid than when it is applied by the processes described in the prior art.

The water dispersible polymer composition is in particulate form. By the term "improved water solubility" is meant that the particulate polymer composition of the present invention has a better water dispersibility than a known particulate polymer composition of the same chemical composition and/or that the particulate polymer composition of the present invention has an equally good water dispersibility at a lower weight ratio between the material which acts as an encrustant and the water-soluble polymer particles than in known compositions. The polymer composition of the present invention has improved water dispersibility at various temperatures, but particularly within a temperature range of 5 to 50° C.

The non-encrusted water-soluble polymer particles generally have a mean particle size of less than 2500 micrometers. They are preferably in the form of a powder of a mean particle size of less than 1000 micrometers, preferably less than 750 micrometers, most preferably less than 500 micrometers. Encrusting the water-soluble polymer particles may lead to agglomeration of the water-soluble polymer particles whereby a granular material is produced. The encrusted water-soluble polymer particles generally have a mean particle size of from 10 to 10,000 micrometers, preferably from 100 to 5,000 micrometers. The term "mean particle size" as used herein means the D[4,3], also designated as equivalent volume mean. $D[4,3]=\Sigma d^4/\Sigma d^3$, wherein the diameter d of a particle is the diameter of a sphere having the same volume as the volume of a given particle. The D[4,3] or equivalent volume mean is measured using a RapidVue 5× image analyzer which is commercially available from Beckman Coulter, Inc., California.

By the present invention particles of a water-soluble polymer are treated. The term "water-soluble" as used herein means that the polymer has solubility in water of at least 2 grams, preferably at least 3 grams, and more preferably at least 5 grams in 100 grams of distilled water at 25° C. and 1 atmosphere.

Preferred water-soluble polymers are homo- or copolymers of ethylene imine, an unsaturated acid, such as acrylic acid or a salt thereof, an unsaturated amide, such as acrylamide, a vinyl polymer, such as vinylalcohol, a vinyl ester, such as vinylacetate, vinylpyrrolidone, vinyloxazolidone, vinylmethyloxazolidone, ethylene sulfonic acid, vinylamine, vinylpyridine, an alkylglycol, a polyalkylene oxide, such as polyethylene oxide, or an oxyethylene alkylether, a gelatin or, most preferably, a polysaccharide.

Examples of polysaccharides include gum arabic, xanthan gum, gum karaya, gum tragacanth, gum ghatti, carrageenan, dextran, alginates, agar, gellan gum, gallactomannans such as guar gum, pectins, starches, starch derivatives, guar derivatives and xanthan derivatives. Starch derivatives, guar derivatives and xanthan derivatives are described in more detail in European patent EP 0 504 870 B, page 3, lines 25-56 and page 4, lines 1-30. Useful starch derivatives are for example starch ethers, such as hydroxypropyl starch or carboxymethyl starch. Useful guar derivatives are for example carboxymethyl guar, hydroxypropyl guar, carboxymethyl hydroxypropyl guar or cationized guar. Preferred hydroxypropyl guars and the production thereof are described in U.S. Pat. No. 4,645,812, columns 4-6. Preferred polysaccharides are cellulose esters or cellulose ethers. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, or alkoxy hydroxyethyl hydroxypropyl celluloses, the alkoxy group being straight-chain or branched and containing 2 to 8 carbon atoms. The most preferred cellulose ethers are methylcellulose, methyl ethylcellulose, hydroxyethyl cellulose, hydroxyethyl ethylcellulose, hydroxypropyl cellulose, hydroxyethyl methylcellulose, hydroxypropyl methylcellulose, and carboxymethyl cellulose, which are classified as water-soluble cellulose ethers by the skilled artisans.

Another preferred polysaccharide is psyllium. The term psyllium is used interchangeably for the seed husk, the seed and the plant. Psyllium seed husk is comprised primarily of xylans. Xylans are polysaccharides built from the five-carbon sugar D-xylose. Xylans in psyllium seed husk occur in association with cellulose. The soluble fiber derived from psyllium seed husk is also known as psyllium hydrophilic mucilloid, psyllium hydrocolloid and psyllium seed gum.

In one aspect of the present invention the water-soluble polymer has a weight average molecular weight of at least 10,000, preferably at least 12,000, more preferably at least 15,000. In another aspect of the present invention the water-soluble polymer has a weight average molecular weight of at least 300,000, preferably at least 400,000, more preferably at least 500,000. In both aspects of the present invention the preferred upper limit for the weight average molecular weight of the water-soluble polymer largely depends on the type of polymer. Generally the weight average molecular weight of the polymer is up to 5,000,000, preferably up to 2,000,000, more preferably up to 1,000,000. The weight average molecular weight can be determined by light scattering according to the Standard Test Method ASTM D-4001-93 (1999). All weight average molecular weights are expressed as grams/mole.

The common principle of the present invention is to contact the water-soluble polymer particles, which are known for their tendency to agglomerate upon wetting with water to form partially hydrated agglomerated polymer particles, with a foamed fluid which comprises a compound that has less tendency to agglomerate. The type of such compound is not very critical provided it has less tendency to agglomerate and can be incorporated in a foamed fluid.

In one aspect of the present invention the water-soluble polymer has a weight average molecular weight of at least 10,000 and a compound A) having a weight average molecular weight of less than 10,000 or a water-insoluble polymer B) having a weight average molecular weight of at least 10,000 serves as an encrustant.

Compound A) has a weight average molecular weight of less than 10,000, preferably less than 5000, more preferably less than 1000. Most preferably compound A) is monomeric. It can be water-soluble or water-insoluble. It can be liquid in its undiluted state at 25° C., however it is preferably solid. Preferred compounds A) are polyglycols, such as polyethylene glycol, polybutylene glycols, methoxypolyethylene glycols or polyglycol copolymers of an above-mentioned molecular weight; compounds useful in mortar, cement, plaster or filler formulations; compounds useful in paint compositions; or preferably compounds suitable for human consumption. Compounds useful in mortar, cement, plaster or filler formulations are, for example, gypsum, mineral oxides, mineral hydroxides, alkali metal chlorides, such as sodium chloride; alkaline earth metal chlorides, such as calcium chloride; clays, metal oxides or hydroxides, quartz sand, quartz rock or silica material, such as ground silica sand or hydrophobic fumed silica; fiber reinforcements, floating agents, plasticizers, surfactants, pigments, wetting agents and/or hydrophobing agents, lightweight additives, such as fly ash, hollow fly ash, hollow ceramic spheres, vermiculite, perlite, calcium silicate hydrate or calcium carbonate. Compounds useful in paint compositions are, for example, silica or pigments like titanium dioxide. Compounds suitable for human consumption are for example edible oils and fats, sodium chloride, maltodextrin or sucrose.

Also water-insoluble polymers B) with a weight average at least 10,000, preferably at least 12,000, more preferably at least 15,000 are useful as encrustants. The upper limit for the weight average molecular weight of the water-insoluble polymers B) is not very critical and is for example up to 10,000,000, typically up to 8,000,000, and usually up to 5,000,000. The term "water-insoluble" as used herein means that the polymer has solubility in water of less than 2 grams, preferably less than 1 gram, in 100 grams of distilled water at 25° C. and 1 atmosphere." The water-insoluble polymers have a decreased tendency to agglomerate and are useful as encrustants for the water-soluble polymers. Preferred water-insoluble polymers are ethyl celluloses and water-insoluble homo- or copolymers of styrene, ethylene, propylene, ethylene terephthalate, acrylates or methacrylates. Preferred water-insoluble homo- or copolymers of acrylates or methacrylates are commercially available under the trademark Eudragit, such as copolymers of methacrylic acid and methyl methacrylate, copolymers of methacrylic acid and ethyl acrylate or polymers of methacrylic acid and dimethylaminoethyl methacrylate.

In another aspect of the present invention the water-soluble polymer has a weight average molecular weight of at least 300,000 and a water-soluble polymer having a weight average molecular weight of less than 100,000 serves as an encrustant. The water-soluble polymers which have a weight average molecular weight of less than 100,000 generally have a decreased tendency to agglomerate, compared to corresponding water-soluble polymer particles having a weight average molecular weight of at least 300,000, and are useful as encrustants for the water-soluble polymer particles of higher molecular weights. Water-soluble polymers which are used as encrustants for higher molecular weight polymers preferably have a weight average molecular weight of 10,000 to less than 100,000, more preferably from 10,000 to 80,000, most preferably from 10,000 to 50,000. In this embodiment of the present invention the water-soluble polymer which is used as an encrustant and the water-soluble polymer particles preferably, but not necessarily, have the same chemical composition apart from their different molecular weights.

If a solid encrustant as described herein is used, its mean particle size, also designated as equivalent volume mean, is preferably up to 5,000 micrometers, more preferably up to 2,000 micrometers.

The amount of the encrustant preferably is from 1 to 60 percent, more preferably from 5 to 50 percent, most preferably from 10 to 40 percent, based on the total weight of the encrustant and the water-soluble polymer particles to be encrusted. Generally the best dispersibility is attained at the higher end of the above-mentioned weight ranges.

To achieve an improved water-dispersibility of the polymer composition it is essential that the fluid composition comprising the encrustant described above is foamed. Accordingly, the fluid composition additionally comprises a foaming agent b) in addition to the above-described encrustant. As described above, the encrustant is a compound A), a water-insoluble polymer B) or a water-soluble polymer having a weight average molecular weight of less than 100,000, depending on the embodiment of the present invention. The fluid composition to be foamed preferably comprises from 1 to 79.99 percent, more preferably from 2 to 70 percent, most preferably from 5 to 50 percent of an above-described encrustant, preferably from 0.01 to 15 percent, more preferably from 0.05 to 10 percent, most from 0.5 to 5 percent of a foaming agent, and preferably from 5 to 98.99 percent, more preferably from 20 to 97.95, most preferably from 45 to 94.95 percent of a liquid diluent, based on the total amount of the fluid composition. The fluid composition may comprise one or more different encrustants and/or one or more different foaming agents, but their total amount is preferably within the ranges stated above.

The term "liquid diluent" means a diluent that is liquid at normal pressure and 25° C. The liquid diluent preferably is a monomeric compound or an oligomeric compound with a molecular weight of up to 500, preferably up to 300. Useful organic liquids are alcohols, preferably monofunctional alcohols, such as ethanol; alkenes, alkanes, halogenated alkenes, halogenated alkanes, ethers, esters or oils, such as paraffin oils, animal oils or vegetable oils. Most preferably, the liquid diluent is water.

The term "foaming agent" as used herein is a compound that enables foaming of the fluid composition described herein when the fluid composition is contacted with a gas, such as oxygen, nitrogen, carbon dioxide or, preferably, air. The produced foam preferably has a foam quality of from 60 to 97 percent, more preferably from 65 to 95 percent, most preferably from 75 to 95 percent. The foam quality FQ is given in percent at atmospheric pressure and 25° C. and is defined as follows:

$$FQ(\%) = [\text{gas volume}/(\text{gas volume} + \text{fluid volume}) \times 100].$$

The foam quality can be measured by measuring the foam volume that is produced from a given volume of fluid at atmospheric pressure and 25° C.

The foaming agent can be an above-described water-soluble polymer. In this case the presence of a foaming agent is generally not directly visible in the dried, non-foamed residue of the foamed fluid on the water-soluble polymer particles but indirectly by comparing the dispersibility of these encrusted water-soluble polymer particles with comparative water-soluble polymer particles encrusted with a comparative encrustant that has been applied as solid or a non-foamed fluid.

In another embodiment of the present invention the foaming agent is a surfactant of a weight-average molecular weight Mw of up to 30000, preferably up to 9000, more preferably up to 5000, even more preferably up to 2000. The most preferred surfactants are non-polymeric compounds with a molecular weight of up to 1000, preferably up to 700.

Surfactants which are useful in the process of the present invention are generally compounds with a hydrophilic head and a hydrophobic end. Anionic, cationic, amphoteric and nonionic surfactants are useful. In many cases nonionic surfactants are preferred over anionic, cationic or amphoteric surfactants.

As anionic surfactants preferably one or more substances from the group of carboxylic acids, carboxylic half-esters, sulfonic acids, preferably from the group of fatty acids, fatty alkylsulfuric acids and alkylarylsulfonic acids; sulfuric acid half-esters of long chain alcohols, alkylethersulfonic acids, like the alkylsulfuric acids; alkanesulfonic acids, or olefinsulfonic acids may be used. Alkali metal salts, preferably the sodium or potassium salts; or ammonium salts of the listed acids are also useful. Accordingly, an alkali metal salt, particularly the sodium salt, is also meant each time in the present description a free acid is mentioned. To achieve adequate surface-active properties, the compounds should have long-chain hydrocarbon radicals, thus have at least 6 carbon atoms in the alkyl or alkenyl radical. Usually the carbon chains in the anionic surfactants contain 6 to 40, preferably 8 to 30, and more preferably 12 to 22 carbon atoms. Preferred carboxylic acids are hexanoic acid (caproic acid), heptanoic acid (enanthic acid), octanoic acid (caprylic acid), nonanoic acid (pelargonic acid), decanoic acid (capric acid), or undecanoic acid. More preferably fatty acids are used, such as dodecanoic acid (lauric acid), tetradecanoic acid (myristic acid), hexadecanoic acid (palmitic acid), octadecanoic acid (stearic acid), eicosanoic acid (arachic acid), docosanoic acid (behenic acid), tetraconsanoic acid (lignoceric acid), hexacosanoic acid (cerotic acid), triacotanoic acid (melissic acid), and the unsaturated species 9c-hexadecenoic acid (palmitoleic acid), 6c-octadecenoic acid (petroselic acid), 6t-octadecenoic acid (petroselaidic acid), 9c-octadecenoic acid (olaic acid), 9t-octadecenoic acid (elaidic acid), 9c,12c-octadecadienoic acid (linoleic acid), 9t,12t-octadecadienoic acid (linolaidic acid), and 9c,12,15c-octadecatrienoic acid (linolenic acid). Also mixtures of fatty acids are useful, such as coconut oil fatty acid, palm kernel oil fatty acid, tallow fatty acid, hardened tallow fatty acids, palmitic/stearic acid mixtures and soybean oil fatty acid. Alkylphosphates, sulfuric acid half-esters of long chain alcohols, alkylethersulfonic acids, like the alkylsulfuric acids; alkanesulfonic acids, olefinsulfonic acids or alkylbenzenesulfonates, preferably linear alkylbenzenesulfonates are also useful anionic surfactants. Alkanesulfonic acids can contain the sulfonic acid group terminally bound (primary alkanesulfonic acids) or along the C chain (secondary alkanesulfonic acids). Fatty alkyl sulfates, such as sodium octyl, decyl, lauryl, tetradecyl, hexadecyl, heptadecyl, or octadecyl sulfate; and salts of alkarylsulfonic acids, such as sodium octylbenzene sulfonates, are preferred. Other useful anionic surfactants are those of the general formula $R(OCH_2CH_2)_nOSO_3M$, wherein R is a $C_{10}$ to $C_{18}$ alkyl group, n is 1 to 3 and M is sodium; and salts of dialkyl sulfosuccinic acids, such as sodium dioctyl sulfosuccinate. A preferred anionic surfactant is sodium lauryl sulfate.

Useful nonionic surfactants are alkoxylated, advantageously ethoxylated, especially primary alcohols with preferably 8 to 18 carbon atoms and an average of 1 to 12 mols ethylene oxide (EO) per mol alcohol, wherein the alcohol radical may be linear or preferably branched in 2-position with methyl, or may contain linear and methyl-branched radicals in a mixture, as customarily occurs in oxoalcohol radicals. In particular, however, alcohol ethoxylates with linear radicals made from alcohols of native origin with 12 to 18 carbon atoms, for example from coconut, palm, tallow fatty, or oleyl alcohols are preferred, and an average of 2 to 8 EO per mol alcohol. Preferred ethoxylated alcohols include, for example, $C_{12-14}$-alcohols with 3 EO or 4 EO, $C_{9-11}$-alcohols with 7 EO, $C_{13-15}$-alcohols with 3 EO, 5 EO, 7 EO or 8 EO, $C_{12-18}$-alcohols with 3 EO, 5 EO or 7 EO and mixtures of these, such as mixtures of $C_{12-14}$-alcohols with 3 EO and $C_{12-18}$-alcohols with 5 EO. The indicated degrees of ethoxylation represent statistical mean values that may be an integer or a fraction for a specific product. In addition to these nonionic surfactants, fatty alcohols with more than 12 EO may also be used. Examples are tallow fatty alcohols with 14 EO, 25 EO, 30 EO or 40 EO. Other preferred nonionic surfactants are ethoxylated reaction products of $C_{8-22}$-fatty alcohols, preferably $C_{12-20}$-fatty alcohols, and especially $C_{14-18}$-fatty alcohols with 1 to 30 mols ethylene oxide, preferably 2 to 20 mols ethylene oxide, and especially 5 to 10 mols ethylene oxide. An additional class of preferably used nonionic surfactants is alkoxylated, preferably ethoxylated or ethoxylated and propoxylated fatty acid alkylesters, preferably with 1 to 4 carbon atoms in the alkyl chain, especially fatty acid methyl esters. An additional class of useful nonionic surfactants is the alkylpolyglycosides (APG). Preferred alkylpolyglycosides have the general formula $RO(G)_z$, in which R represents a linear or branched, especially methyl-branched in 2-position, saturated or unsaturated aliphatic radical with 8 to 22, preferably 12 to 18 C-atoms and G is the symbol that represents a glycose unit with 5 or 6 C-atoms, preferably glucose. The glycosidation degree z here is from 1.0 to 4.0, preferably from 1.0 to 2.0, and especially from 1.1 to 1.5. Preferably used are linear alkylpolyglucosides, thus alkylpolyglycosides in which the polyglycol radical is a glucose radical and the alkyl radical is an n-alkyl radical. An additional class of suitable nonionic surfactants are polyhydroxy fatty acid amides of Formula $R-CO-N(R^1)-[Z]$, wherein R—CO represents an aliphatic acyl radical with 6 to 22 carbon atoms, $R^1$ represents hydrogen, an alkyl or hydroxyalkyl radical with 1 to 4 carbon atoms and [Z] represents a linear or branched polyhydroxyalkyl radical with 3 to 10 carbon atoms and 3 to 10 hydroxyl groups.

Useful cationic surfactants have cationic hydrophobic residues and counter-cations, such as chloride, sulfate, or acetate. Examples include tetraalkyl ammonium chlorides, aryl trialkyl ammonium chlorides, tetraalkyl ammonium bromides, aryl trialkyl ammonium bromides or N-alkylpyridinium chloride.

Amphoteric surfactants have zwitterionic hydrophilic groups. Examples thereof include aminocarboxylic acids, betaines, and sulfobetaines.

Generally a physiologically acceptable surfactant is used in the process of the present invention. Preferably the fluid composition which is used in step i) of the process of the present invention comprises a benzalkonium chloride (alkyl benzyl dimethylammonium chloride, CAS Registration number [8001-54-5]); cetrimide (hexadecyltrimethyl ammonium bromide, CAS Registration number [8044-71-1]); a glyceryl monooleate; a glyceryl monostearate; a glyceryl palmitostearate, CAS Registration number [8067-32-1]; a poloxamer (a polyethylene glycol, CAS Registration number [9003-11-6]); a polyoxyethylene alkyl ether, a polyoxyethylene castor oil derivative, a polyoxyethylene sorbitane fatty acid ester, such as a poly(oxyethylene)-sorbitane monooleate; a polyoxyethylene stearate, a sorbitane fatty acid ester, such as a sorbitane monooleate; and sodium lauryl sulfate, or a combination of two or more of the listed surfactants.

The fluid composition is contacted with a gas, such as oxygen, nitrogen, carbon dioxide or, preferably, air to produce a foam. Preferably water-based air foam is produced. The term "air foam" is used in its industry-accepted sense to mean foam made by physically mixing air into a fluid, and thus the term is distinct from chemical or carbon dioxide foam or halocarbon blown foam. The foam can be produced in a known manner by mechanically or physically entraining or dispersing the gas in the fluid composition, for example by pumping the fluid composition to air-aspirating, foam producing equipment. The produced foamed fluid comprises a discontinuous gas phase, preferably an air phase, and a continuous fluid phase, preferably an aqueous phase, comprising the above-described encrustant, the foaming agent and the bound liquid.

The foamed fluid can be contacted with the water-soluble polymer particles in a known manner. The foamed fluid and the water-soluble polymer particles are preferably chosen in such amounts that the above-mentioned weight ratios between the above-described surfactant and the water-soluble polymer particles are achieved. Advantageously known mixing devices are used, such as a high shear mixing device, a low shear mixing device, a fluidized bed granulator, a roller compactor or a spray dryer. The contacting step is followed by a drying step which can be conducted in a known manner. The foam lamellae break during the contacting and/or the drying step whereby the foam collapses and the water-soluble polymer particles are encrusted with the above-described surfactant. The water-soluble polymer particles are generally granulated upon contact with the foamed fluid composition. The produced, generally granular, material can be subjected to one or more known compounding steps, such as grinding, for example wet-milling or dry-milling, sieving and/or mixing with optional ingredients.

The water-dispersible polymer composition comprising the above-described encrusted water-soluble polymer particles may comprise a wide variety of additional, optional ingredients, depending on the desired end-use of the composition. Exemplary thereof are pharmaceutical excipients, such as lactose, dicalcium phosphate, sugars, artificial sweeteners, minerals, disintegrants, binders, lubricants, colorants, flavorants, drugs or combinations thereof or drugs. Other useful optional ingredients are known additives for mortar, cement, plaster or filler compositions, such as Portland cement or alumina cement or known additives for paint compositions.

The water dispersible polymer composition of the present invention is particularly useful in pharmaceutical compositions, preferably in hard-shell capsules or in bulk laxatives; in food compositions; in mortar, cement, plaster or filler compositions for the building industry, in paint compositions, in ink compositions, and in compositions which are used in the oil field and mining industry, such as viscosified brine solutions which comprise a water-soluble polymer as a viscosifying agent.

The drying step can be carried out prior to or after the optional grinding step. The optional grinding step and/or the optional step of mixing with one or more optional ingredients can be conducted before, during or after the drying step.

The polymer composition of the present invention is in particulate form and has improved water dispersibility at various temperatures, but particularly within a temperature range of 5 to 50° C. The particulate polymer composition of the present invention has a better water dispersibility than a known particulate polymer composition of the same chemical composition and/or the particulate polymer composition of the present invention has equally good water dispersibility at a lower weight ratio between the above-described encrustant and the water-soluble polymer particles than in known compositions.

Some water-soluble polymer particles, particularly water-soluble cellulose derivatives, are commonly used as thickening agents in various aqueous compositions, such as paint compositions, ink compositions, liquid food compositions, pharmaceutical liquid preparations, liquid mortar, cement, plaster or filler compositions for the building industry, and in liquid compositions which are used in the oil field and mining industry. It has surprisingly been found that in preferred embodiments of the present invention not only the water dispersibility of water-soluble polymer particles can be further improved when the polymer particles are encrusted with a dried, non-foamed residue of a foamed encrustant as described herein but that also the time period between the addition of the water-soluble polymer particles to an aqueous composition and the resulting elevated viscosity in the aqueous composition and/or the hydration time (the time period from when the viscosity starts to increase upon addition of the water-soluble polymer particles and the point in time when the increased viscosity remains constant) can be influenced. Influencing this time period is very favorable since it improves the handling properties of the aqueous composition.

The present invention is further illustrated by the following examples which should not be construed to limit the scope of the present invention. All parts and percentages are by weight unless otherwise indicated. The alkyl and hydroxyalkyl substitutions of the cellulose ethers indicated in the examples below are measured and calculated according to ASTM D3876. The apparent viscosities indicated in the examples below are measured and normalized to a 2 weight percent aqueous solution using an Ubbelohde viscometer at 20° C.

EXAMPLES

The compounds used in the Examples and Comparative Examples are listed in Table 1.

TABLE 1

| Designation | Description |
|---|---|
| A4M (water-soluble polymer particles) | Methylcellulose having a methoxyl content of 27.5-31.5 percent and a viscosity of about 4,000 mPa · s. It is commercially available from The Dow Chemical Company under the Trademark METHOCEL A4M Premium Grade. |
| K4M | Hydroxypropyl methylcellulose with a methoxyl substitution of 19-24 |

TABLE 1-continued

| Designation | Description |
|---|---|
| (water-soluble polymer particles and foaming agent) | percent, a hydroxypropoxyl substitution of 7-12 percent and a viscosity of about 4,000 mPa · s. It is commercially available from The Dow Chemical Company under the Trademark METHOCEL K4M Premium Grade. |
| J75MS-N (water-soluble polymer particles) | Hydroxypropyl methylcellulose with a methoxyl substitution of 16.5-20 percent, a hydroxypropoxyl substitution of 24-32 percent and a viscosity of about 75,000 mPa · s. It is surface-treated with the cross-linking agent glyoxal to achieve a good dispersibility in water at a pH of below about 8.5. It is commercially available from The Dow Chemical Company under the Trademark METHOCEL J75MS-N. |
| 856N (water-soluble polymer particles) | A non-surface-treated hydroxypropyl methylcellulose with a methoxyl substitution of 16.5-20 percent, a hydroxypropoxyl substitution of 24-32 percent and a viscosity of about 75,000 mPa · s. |
| E3 (water-soluble polymer particles and foaming agent) | Hydroxypropyl methylcellulose with a methoxyl substitution of about 29 percent, a hydroxypropoxyl substitution of about 9 percent and a viscosity of 3 mPa · s. It is commercially available from The Dow Chemical Company under the Trademark METHOCEL E3 Premium Grade. |
| HEC 52M (water-soluble polymer particles) | Hydroxyethyl cellulose having a 1% Brookfield viscosity of 2400-3000 cp (mPa.s) according to ASTM D-2364. It is surface-treated with the cross-linking agent glyoxal to achieve a good dispersibility in water at a pH of below about 8.5 and 1% fumed silica which is added to prevent caking in storage. It is commercially available from The Dow Chemical Company as Cellosize ER 52M hydroxyethyl cellulose and is commonly used as a thickener in latex paints where paint formulators want an HEC polymer with high thickening efficiency. |
| HEC (water-soluble polymer particles) | Non-modified hydroxyethyl cellulose which has the same hydroxyethoxyl substitution and the same Brookfield viscosity as HEC 52M, but it is not cross-linked with glyoxal and does not contain fumed silica. |
| A15 (foaming agent) | Methylcellulose having a methoxyl content of 27.5-31.5 percent and a viscosity of about 15 mPa · s. It is commercially available from The Dow Chemical Company under the Trademark METHOCEL A15 Premium Grade. |
| SLS (foaming agent) | Sodium lauryl sulfate surfactant |
| K3 (foaming agent) | Hydroxypropyl methylcellulose with a methoxyl substitution of 19-24 percent, a hydroxypropoxyl substitution of 7-12 percent and a viscosity of 3 mPa · s. It is commercially available from The Dow Chemical Company under the Trademark METHOCEL K3 Premium Grade. |
| PEG 400 (foaming agent) | Polyethylene glycol with a weight average molecular weight of about 400 |
| PEG 8000 (foaming agent) | Polyethylene glycol with a weight average molecular weight of about 8000 |
| Calcium carbonate (encrustant) | Calcium carbonate micro white, (average particle size 18 micron), commercially available from Imerys, USA |
| Ti-Pure 900 (encrustant) | Average particle size 0.41 micron, commercially available from DuPont. Contents: 94% titanium Dioxide, 4.3% alumina |
| Ti-Pure 931 (encrustant) | Average particle size 0.55 micron, commercially available from DuPont. Contents: 80% titanium Dioxide, 6.4% alumina, 10.2% silica |

Examples 1-9 and Comparative Examples A and B

Aqueous fluids were produced with the ingredients listed in Table 2 below. They contained sucrose or maltodextrin as compound A) described further above and A15 or SLS as a foaming agent. The remaining amount was water. The aqueous fluid was foamed in a known manner by contacting the fluid with an air stream. A method of generating foam is described in the International Patent Publication WO 03/020244. In Examples 1-9 a foamed fluid with the composition listed in Table 2 below was contacted with 500 g of water-soluble polymer particles A4M in powder form at a rate of 100 m/min in a high shear granulator. The ratio between the water-soluble polymer particles and the sucrose or maltodextrin was controlled by the time period of adding the foamed fluid to the water-soluble polymer particles. The water-soluble polymer particles A4M were granulated.

Comparative Examples A and B were carried out as Examples 1-9, except that the foamed fluid did not contain sucrose or maltodextrin. In Comparative Examples A and B 500 g of water-soluble polymer particles A4M had been pre-blended in dry state either with 250 g of maltodextrin or 250 g of sucrose. The dry blends were granulated upon contact with the foamed fluid in the high shear granulator. The granules were dried in a fluid bed at 90° C. for ten minutes.

Comparative Examples C and D

In Comparative Example C the water-soluble polymer particles A4M were encrusted with sucrose at a weight ratio of 2:1. Sucrose was added as hot syrup to the water-soluble polymer particles as taught in U.S. Pat. No. 4,671,823.

In Comparative Example D the water-soluble polymer particles A4M were encrusted with maltodextrin at a weight ratio of 2:1. Maltodextrin was added as a hot aqueous solution.

TABLE 2

| (Comp.) Example | Powder composition | Foamed fluid, concentration based on total solution (%) | | | | Methyl cellulose | Encrustant (sucrose or maltodextrin) |
|---|---|---|---|---|---|---|---|
| | | Sucrose | Maltodexrin | SLS | A15 | | |
| 1 | 500 g A4M | 40 | 0 | 0 | 1.2 | 71.7 | 28.3 |
| 2 | 500 g A4M | 25 | 0 | 0 | 1.5 | 83.5 | 16.5 |
| 3 | 500 g A4M | 14.3 | 0 | 0 | 1.7 | 91.0 | 9.0 |
| A* | 500 g A4M + 250 g sucrose | 0 | 0 | 0 | 2 | 66.8 | 33.2 |
| B* | 500 g A4M + 250 g maltodextrin | 0 | 0 | 0 | 2 | 66.8 | 33.2 |
| 4 | 500 g A4M | 0 | 37.4 | 0.4 | 0 | 72.6 | 27.1 |
| 5 | 500 g A4M | 0 | 25 | 0.4 | 0 | 83.1 | 16.6 |
| 6 | 500 g A4M | 0 | 14.3 | 0.4 | 0 | 90.7 | 9.1 |
| 7 | 500 g A4M | 0 | 25 | 0 | 0.8 | 82.9 | 16.6 |
| 8 | 500 g A4M | 0 | 14.3 | 0 | 0.8 | 90.4 | 9.0 |
| 9 | 500 g A4M | 0 | 7.7 | 0 | 0.8 | 94.8 | 4.7 |
| C | A4M encrusted with sucrose at a ratio 2:1, sucrose added as hot syrup | | | | | 66.7 | 33.3 |
| D | A4M encrusted with maltodextrin at a ratio of 2:1, maltodextrin added as a hot aqueous solution | | | | | 66.7 | 33.3 |

*Not an Example of the Invention but not prior art

The produced water dispersible polymer compositions of Examples 1-9 and Comparative Examples A-D were visually inspected. A tablespoon of each of the polymer compositions was dispersed in a glass of water at room temperature and its water dispersibility was visually inspected by 7 persons. There was no divergence in opinions about the results of the visual inspection.

The compositions of Examples 1, 4 and 7 showed the best water dispersibility of all runs listed in Table 2. The polymer compositions produced a negligible quantity of fish-eyes and were very easily mixed into water at room temperature.

The compositions of Examples 2 and 5 respectively showed a water dispersibility that was only slightly inferior to the water dispersibility of the compositions of Examples 1 and 4 respectively.

The compositions of Examples 3, 6, 8 and 9 showed a water dispersibility that was inferior to the water dispersibility of the compositions of Examples 1, 2, 4, 5 and 7 but still better than the water dispersibility of the compositions of Comparative Examples C and D. The better water dispersibility is surprising since the compositions of Examples 3, 6, 8 and 9 have a much smaller amount of encrustant than the compositions of Comparative Examples C and D.

The compositions of Comparative Examples C and D showed the least satisfactory water dispersibility. Lumps of high viscosity, some as large as a tea spoon, were formed. Non-wetted powder was still visible after stirring.

The compositions of Comparative Examples A and B showed only a slightly better water dispersibility than the compositions of Comparative Examples C and D. However, the dispersibility of the compositions of Comparative Examples A and B was inferior to the dispersibility of the compositions of Examples 1, 2, 4, 5 and 7 and not significantly better than the dispersibility of the compositions of Examples 3, 6, 8 and 9. This is surprising since the compositions of Examples 3, 6, 8 and 9 have a much smaller amount of encrustant than the compositions of Comparative Examples A and B.

Examples 10-16

Aqueous fluids were produced with the ingredients listed in Table 3 below, the remaining amount being water. The aqueous fluid composition was foamed and contacted with the powder particles as in Examples 1-9.

TABLE 3

| (Comp.) Example | Powder | Foamed fluid, concentration based on total solution (%) | | | | | % PEG, based on total amount of encrusted particles |
|---|---|---|---|---|---|---|---|
| | | K3 | K4M | PEG 400 | E3 | PEG 8000 | |
| 10 | E3 | 1 | — | 50 | — | — | 14.2 |
| 11 | E3 | — | — | — | 0.5 | 12.5 | 3.2 |
| 12 | E3 | — | — | 40 | 1.2 | — | 10.0 |
| 13 | E3 | — | — | 51.5 | 1.0 | — | 15.0 |
| 14 | E3 | — | — | 24 | 1.5 | — | 5.0 |
| Comp. E | E3 | — | — | — | — | — | — |
| 15 | K4M | — | 0.5 | 38.5 | — | — | 17.0 |
| 16 | K4M | 1 | — | 50 | — | — | 14.2 |
| Comp. F | K4M | — | — | — | — | — | — |

The water dispersibility of the produced encrusted particles was visually inspected as in Examples 1-9. All Examples 10-14 showed better water dispersibility than Comparative Example E. Examples 10 and 12-14 created some gel bodies upon dispersion in water which disappeared in 1-2 hours under gentle agitation. Examples 15 and 16 showed better water dispersibility than Comparative Example F. The best water dispersibility was achieved with the composition of Example 15; it was easily dispersible in water and left only very small visible gel bodies in water. Example 11 created a gel layer consisting mainly of PEG 8000 below the aqueous solution of the water-soluble polymer.

Examples 17-18 and Comparative Examples G-H

Aqueous fluids were produced with the ingredients listed in Table 4 below. They contained calcium carbonate ($CaCO_3$) or maltodextrin as compound A) described further above and K3 or SLS as a foaming agent. The remaining amount was water. The aqueous fluid of Example 18 contained slurried calcium carbonate. It could be foamed in a commercial HANSA foam generator. The foamed aqueous fluid compositions were contacted with the powder particles as in Examples 1-9.

TABLE 4

| (Comp.) Example | Powder composition | Foamed fluid, concentration based on total solution (%) | | | | % of encrustant, based on total amount of encrusted particles Maltodextrin or Calcium Carbonate |
|---|---|---|---|---|---|---|
| | | K3 | SLS | Malto-dexrin | Calcium carbonate | |
| 17 | 856N | — | 0.4 | 14.3 | — | 9.1 |
| 18 | 856N | 1 | — | — | 15 | 9.4 |
| G | 856N, not contacted with a foamed fluid | | | | | |
| H | J75MS-N, surface-treated with glyoxal to achieve good dispersibility in water, not contacted with foamed fluid | | | | | |

The water dispersibility of the produced encrusted particles of Examples 17 and 18, of the non-surface-treated hydroxypropyl methylcellulose 856N of Comparative Example G and of the surface-treated hydroxypropyl methylcellulose METHOCEL J75MS-N of Comparative Example H were visually inspected and compared. 1.8 g of each of the polymer particles were dispersed in 900 ml of water by mechanical stirring at 250 RPM (revolutions per minute) at 21 degree Celsius.

The encrusted particles of Examples 17 and 18 and the surface-treated particles of Comparative Examples H showed equally good dispersibility. A smooth and uniformly moist aqueous composition of high viscosity was obtained without noticeable formation of lumps.

The particles of Comparative Example G showed significantly inferior water dispersibility. The obtained aqueous composition was much less smooth, not uniformly moist and showed areas of non-wetted material.

Examples 19-25 and Comparative Examples I and J

A 1 percent aqueous K3 solution was prepared. The inorganic materials listed in Table 5 were charged into separate samples of the K3 solutions to produce slurries which had the compositions listed in Table 5. A commercial HANSA foam generator was used to foam the slurries. The foamed fluids were contacted with 500 g of unmodified HEC or with HEC 52M in a high shear granulator. The rate of foam addition to the powder bed was 200 grams per minute. The ratio between the polymer particles and the inorganic materials was controlled by the amount of insoluble material suspended in solution and the time period of foam addition. The prepared granules were spread on a tray and oven dried at 38° C. (100 F) for 20 hours. The samples were cooled to room temperature and milled using a Co-mil at 1000 rpm through a 12 mesh screen size (less than 1700 micron size particles).

TABLE 5

| (Comp.) Example | Powder | Foamed fluid, concentration based on total solution (%) | | | | Foamed fluid, concentration based on total solution (%) |
|---|---|---|---|---|---|---|
| | | Ti-Pure 931 | Ti-Pure 900 | Calcium Carbonate | K3 | Ti-Pure 931, or Ti-Pure 900, or Calcium carbonate |
| 19 | HEC | | | 15 | 1 | 9.4 |
| 20 | HEC | | | 2 | 1 | 1.4 |
| 21 | HEC | | 15 | | 1 | 9.4 |
| 22 | HEC | 15 | | | 1 | 9.4 |
| 23 | HEC 52M | | | 15 | 1 | 9.4 |
| 24 | HEC 52M | | | 2 | 1 | 1 |
| 25 | HEC 52M | 15 | | | 1 | 1 |
| I | HEC, not surface-treated, not foamed, not contacted with foamed fluid | | | | | |
| J | HEC 52M, surface-treated with glyoxal to achieve good dispersibility, not contacted with foamed fluid | | | | | |

Dispersibility in Water

The water dispersibility of the produced encrusted particles of Examples 19-25 was visually inspected and compared with the water dispersibility of "as received" samples of Comparative examples I and J at 22° C. and 50% humidity. 4 grams of each of the polymer particles were dispersed in 196 grams of water by mechanical stirring (160 rpm). The foam encrusted particles of Examples 19-25 and the surface treated HEC 52M of Comparative Example J showed equally good dispersibility. The encrusted granules remained separate when added to water. The granules did not clump together and remained suspended while the solution viscosity increased. A high viscosity solution was obtained without noticeable lumps. The particles of the non-treated HEC of Comparative Example I showed significantly inferior dispersibility. The particles immediately formed large lumps that gelled on the exterior and contained non-wetted material and did not disperse.

Hydration Time in Water

The hydration time of the produced encrusted particles of Examples 19-25 and of "as received" samples of Comparative examples I and J was measured at 22° C. and 50% humidity. 4 grams of each of the polymer particles were dispersed in 196 grams of water by mechanical stirring (160 rpm). The time when the viscosity started to increase (T1) and the point in time when the viscosity remained constant (T2) were measured and recorded using a C.W. Brabender viscometer. For Examples 23-25 the time period T2-T1 was significantly shorter than that of the non-encrusted particles of Comparative Example J. The time period T2-T1 is designated herein as "hydration time". The hydration times of Examples 23-25 were up to 95 percent faster. The hydration times of HEC 52M encrusted with calcium carbonate (Examples 23 and 24) were the fastest, followed by the hydration time of the encrusted particles of Example 26.

Although the produced encrusted particles of Examples 19-22 dispersed very easily, the hydration times were difficult to measure. The viscosity increase was almost immediate and then continued at a gradual rate (still increasing after 1.5 hours). The particles of Example 19 were separated into two samples with particle sizes of at least 600 micrometers and particles of less than 600 micrometers. Then the hydration times were examined. The particles of less than 600 micrometers dispersed easily in water at 22° C. without the formation of lumps and showed very fast hydration times. The particles of more than 600 micrometers also dispersed easily in water at 22° C. without the formation of lumps and showed long hydration times. It was not possible to measure comparable hydration times for the HEC particles of Comparative Example I due to the inability of the particles to disperse at 22° C. in water. The large gelled clumps created too much noise in the recorded data.

What is claimed is:

1. A process for producing a water dispersible polymer composition comprising the steps of
   i) foaming a fluid composition comprising a foaming agent and a water insoluble compound A) having a weight average molecular weight of less than 10,000 or a water-insoluble polymer having a weight average molecular weight of at least 10,000, wherein the fluid composition does not include sugars;
   ii) contacting the produced foam with water-soluble polymer particles having a weight average molecular weight of at least 10,000 selected from water-soluble carboxy-$C_1$-$C_3$-alkyl cellulose, carboxy-$C_1$-$C_3$-alkyl hydroxy-$C_1$-$C_3$-alkyl cellulose, $C_1$-$C_3$-alkyl cellulose, $C_1$-$C_3$-alkyl hydroxy-$C_{1-3}$-alkyl cellulose, hydroxy-$C_{1-3}$-alkyl cellulose, mixed hydroxy-$C_1$-$C_3$-alkyl cellulose, or mixed $C_1$-$C_3$-alkyl cellulose; and
   iii) drying the particles, whereby the foam collapses during the contacting and/or drying step and the water-soluble polymer particles are encrusted with the compound A) or the water-insoluble polymer B).

2. The process of claim 1 wherein the water-soluble polymer particles are encrusted with calcium carbonate or titanium dioxide.

3. The process of claim 1 wherein the water-insoluble polymer B) is an ethyl cellulose or a water-insoluble homo- or copolymer of styrene, ethylene, propylene, (meth)acrylate or ethylene terephthalate.

4. The process of claim 1, wherein compound A) is gypsum, mineral oxides, clays, metal oxides, quartz, silica, titanium dioxide, fly ash, hollow fly ash, hollow ceramic spheres, vermiculite, perlite, calcium silicate hydrate or calcium carbonate.

* * * * *